United States Patent
Pettus, IV et al.

(10) Patent No.: US 10,595,843 B2
(45) Date of Patent: Mar. 24, 2020

(54) RETRACTION SYSTEM AND METHOD

(71) Applicants: Joseph Atkins Pettus, IV, Madison, AL (US); Tristan Reilly Pettus, Madison, AL (US)

(72) Inventors: Joseph Atkins Pettus, IV, Madison, AL (US); Tristan Reilly Pettus, Madison, AL (US)

( * ) Notice: Subject to any disclaimer, the term of this patent is extended or adjusted under 35 U.S.C. 154(b) by 44 days.

(21) Appl. No.: 16/027,462

(22) Filed: Jul. 5, 2018

(65) Prior Publication Data

US 2019/0133566 A1    May 9, 2019

Related U.S. Application Data

(60) Provisional application No. 62/529,670, filed on Jul. 7, 2017.

(51) Int. Cl.
| | | |
|---|---|---|
| *A61B 1/32* | (2006.01) | |
| *A61B 17/02* | (2006.01) | |
| *A61B 17/34* | (2006.01) | |
| *A61B 17/00* | (2006.01) | |
| *A61B 1/313* | (2006.01) | |

(52) U.S. Cl.
CPC ...... *A61B 17/0218* (2013.01); *A61B 17/3423* (2013.01); *A61B 1/3132* (2013.01); *A61B 2017/00367* (2013.01); *A61B 2017/00477* (2013.01); *A61B 2017/0225* (2013.01); *A61B 2017/347* (2013.01)

(58) Field of Classification Search
CPC combination set(s) only.
See application file for complete search history.

(56) References Cited

U.S. PATENT DOCUMENTS 5,263,969 A * 11/1993 Phillips ............... A61F 2/0063
                                                        606/1

* cited by examiner

*Primary Examiner* — Sameh R Boles
(74) *Attorney, Agent, or Firm* — Cygnet IP Law, P.A.; Stephen W. Aycock, II

(57) ABSTRACT

Some implementations can include a retraction system that provides broad based retraction for minimally invasive procedures (e.g., laparoscopic or robot-assisted) similar to that achieved by fixed retractors often used in open surgery. The retraction system can hold viscera out of the pelvis, for example. Some implementations can include a first instrument, a first locking trocar, a second instrument, and a second locking trocar. The first instrument can include an articulated first device having a mesh net. The first device is capable of unfurling the mesh net and winding the net back up into the first device. The second instrument can include a second device that articulates and engages an edge of the mesh net. The second device can engage the mesh net and assist in unfurling the mesh net by pulling the mesh net so that the mesh net unwinds from the first device and can be used to retract the viscera.

1 Claim, 8 Drawing Sheets

RETRACTION SYSTEM AND METHOD

RELATED APPLICATIONS

This application claims the benefit of U.S. Provisional Application No. 62/529,670, entitled "Retraction System and Method," and filed on Jul. 7, 2017, which is incorporated herein by reference in its entirety.

TECHNICAL FIELD

Some implementations relate generally to surgical instruments, and more particularly, to a retraction system and method for laparoscopic and/or robot-assisted pelvic surgery and other minimally invasive surgeries.

BACKGROUND

Currently, laparoscopic and/or robot-assisted pelvic surgeries may often require steep Trendelenburg positioning in which a patient being operated upon is placed in a head down position at an angle of about 45 degrees for the duration of the procedure. Such positioning may be necessary to move viscera out of the pelvis so as to provide adequate visualization and exposure of the operative field.

Trendelenburg positioning may suffer some one or more limitations or disadvantages, such as making ventilation of the patient more difficult for the anesthesia staff. Also, patients may need to be padded and securely fastened to the table adding time and therefore cost to the procedure. Further, Trendelenburg positioning has occasionally resulted in complications such as cerebral edema, neurologic complications, lower extremity ischemia, among other adverse events.

Accordingly, a need may exist for a system and method of viscera retraction that involves limited or no Trendelenburg positioning.

Some implementations were conceived in light of the above mentioned needs and limitations, among other things.

SUMMARY

Some implementations can include a retraction system that can reduce use of Trendelenburg positioning to a few minutes and may eliminate the use of Trendelenburg positioning altogether.

Some implementations can include a laparoscopic retraction system that provides broad based retraction similar to that achieved by fixed retractors routinely used in open surgery. The laparoscopic retraction system can hold viscera out of the pelvis so that laparoscopic or robot-assisted pelvic operations can be performed with little or no Trendelenburg positioning required. Some implementations can include a first instrument and a corresponding first locking trocar and a second instrument and a corresponding second locking trocar.

The first (or "male") instrument can include a first device having a mesh net rolled up within the device. The first device is capable of unfurling the mesh net and winding the net back up into the first device. The unfurling and winding up can be controlled by a net control knob located on the external end of the first instrument (i.e. outside the patient's body) and mechanically or electrically coupled to the net winding mechanism located toward the end of the instrument which unfurls and winds up the mesh net. The first locking trocar can be a trocar selected to provide a port of about 5-7 mm, 12 mm or other suitable dimension. The first instrument can also include an articulation control knob to control articulation of the end of the first instrument inside the patient's body when the first instrument is in use during a procedure. The articulation control knob and the net control knob can include separate control knobs. Both articulation control knobs are disposed on respective portions of the first or second instruments that are external to the patient when the instruments are in use during a procedure.

The second (or "female") instrument can include a second device that is capable of articulating and engaging an edge of the mesh net being unfurled from the first device. The articulation can be controlled by an articulation control knob on the second instrument, where the articulation control knob of the second instrument is disposed on a portion of the second instrument that is external to the patient when the instrument is in use during a procedure. The second device can be used to engage the mesh net and unfurl the mesh net by pulling the mesh net so that the mesh net unwinds from the first device and extends from side to side across the peritoneum. The two instruments can then be positioned and locked into place by the respective locking trocars in order to cause the mesh net to retract and hold the viscera out of the pelvis during a procedure without further attention from the surgical assistant. The second trocar can be a trocar selected to provide a port of about 5 mm.

DETAILED DESCRIPTION

Figure 1:
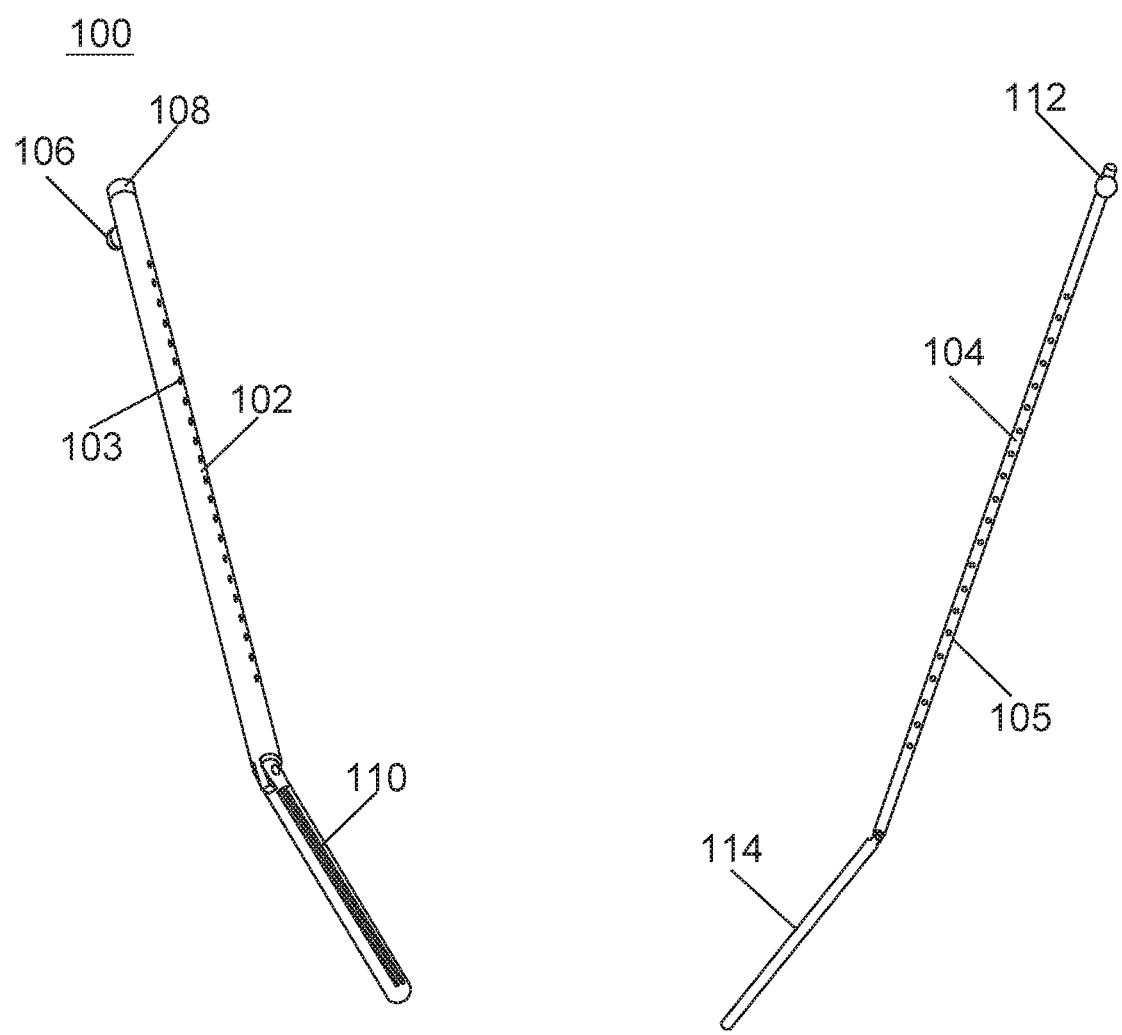
FIG. 1 is a diagram of example first ("male") and second ("female") instruments of a retraction system in accordance with some implementations.

FIG. 1 is a diagram of an example first instrument 102 and second instrument 104 of a retraction system 100 in accordance with some implementations. The first instrument 102 (e.g., instrument placed through a 5-7 mm port or a 12 mm port or port of other suitable dimensions) includes one or more holes 103 in the shaft of the instrument, an articulation control knob 106, a net control knob 108, and an articulated end 110 that can move in response to control movements of the articulation knob 106 and which holds a wound up retraction mesh net 206 shown in FIG. 2. The second instrument 104 includes one or more holes 105 in the shaft of the instrument, an articulation control knob 112 and an articulated end 114.

In operation, two additional ports are placed superior to the "working" ports. The two additional ports can include a first port (e.g., a port for the 5 mm-7 mm or 12 mm "male"

instrument that deploys the mesh net) and a second port (e.g., a port for the "female" instrument that accepts and engages the mesh net and locks it into place) formed by respective locking trocars, for example. The first instrument 102 containing the rolled up retractor mesh net (or other suitable retractor material) is placed into the first port provided by the first trocar and the mesh net is unrolled from it. The mesh net is engaged (or captured) by an articulated end 114 of the second instrument 104 that has been placed through the second port 204. The net is then tensioned by rolling it up using the furling knob 108 on the first instrument 102 and can be articulated to precisely retract the viscera superiorly and out of the operative field. A brief time (e.g., 5 minutes) of Trendelenburg positioning time may be required to get the retraction system in place and positioned. Once satisfactory retraction is achieved, the trocars (202 and 204) can lock the two instruments (102, 104) in place via one or more holes on the instruments (103, 105) and may not require further attention by the assistant. The patient can be returned to level positioning and the operation can proceed as usual. A diagram of a deployed retraction system in accordance with some implementations is shown in FIG. 2.

Figure 2:
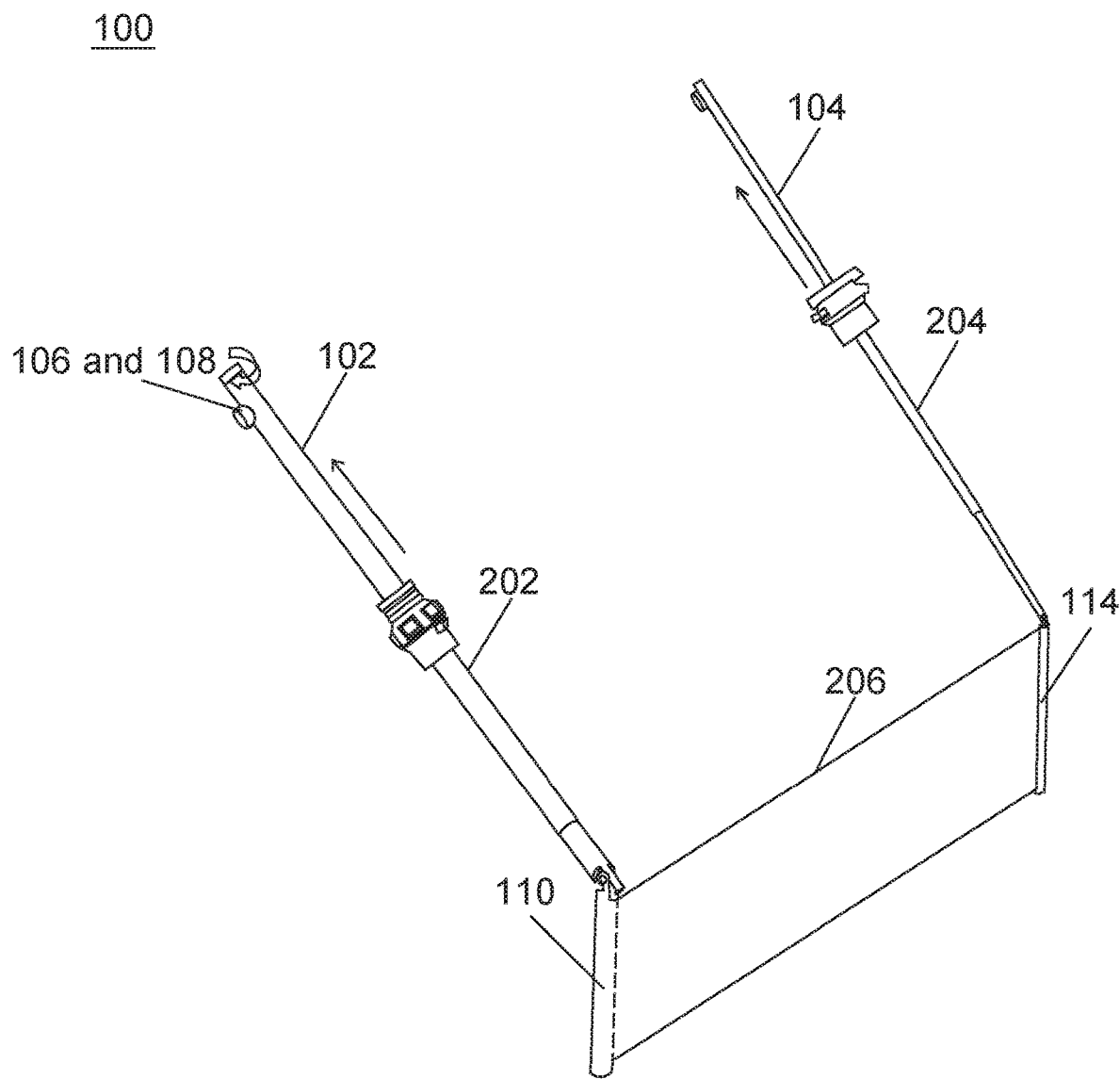
FIG. 2 is a diagram of an example retraction system with the mesh net deployed in accordance with some implementations.

FIG. 2 is a diagram of an example retraction system 100 with the mesh net 206 deployed in accordance with some implementations. In particular, the first instrument 102 is placed through a first trocar 202 and the second instrument 104 is placed through a second trocar 204. The retractor shown in FIG. 2 is in a locked state.

Figure 3:
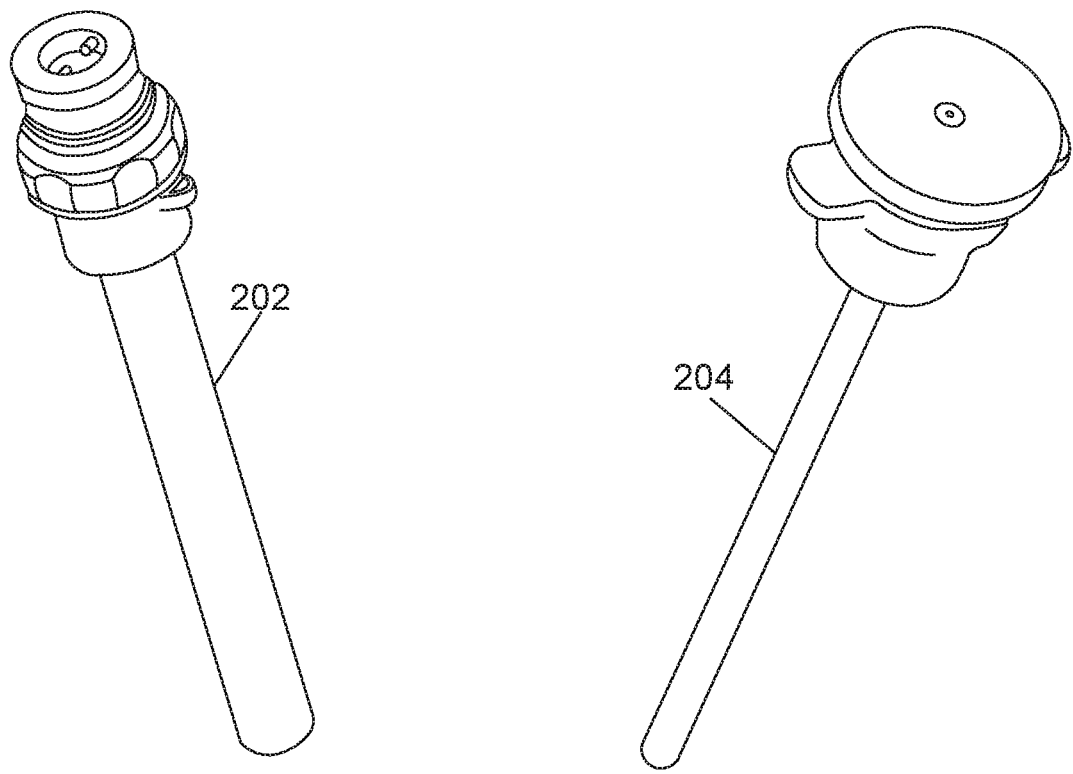
FIG. 3 is a diagram of example locking trocars in accordance with some implementations.
Figure 6:
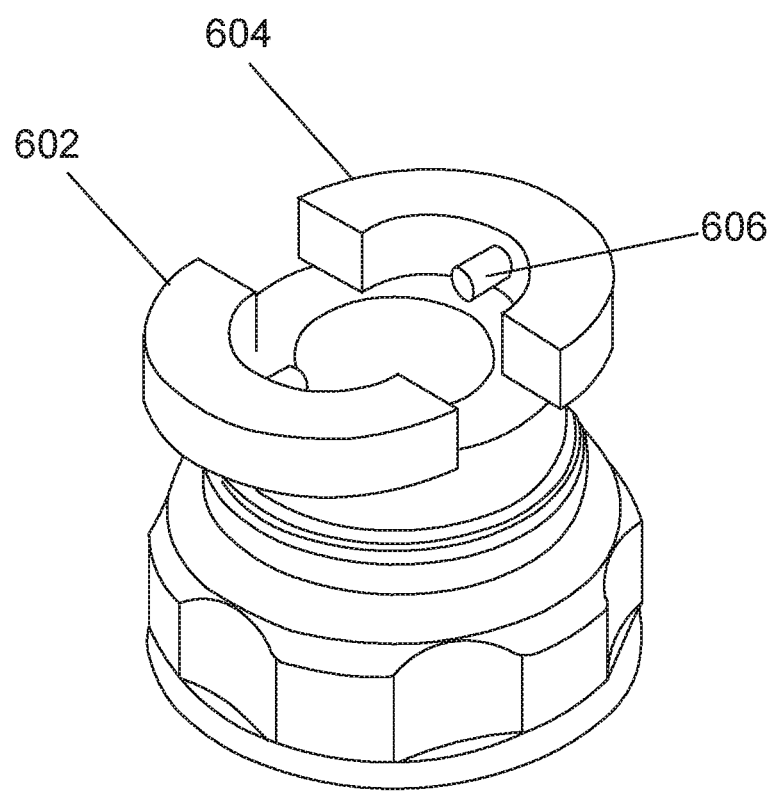
FIG. 6 is a diagram of an external end of an example locking trocar for the "male" instrument in accordance with some implementations.
Figure 7:
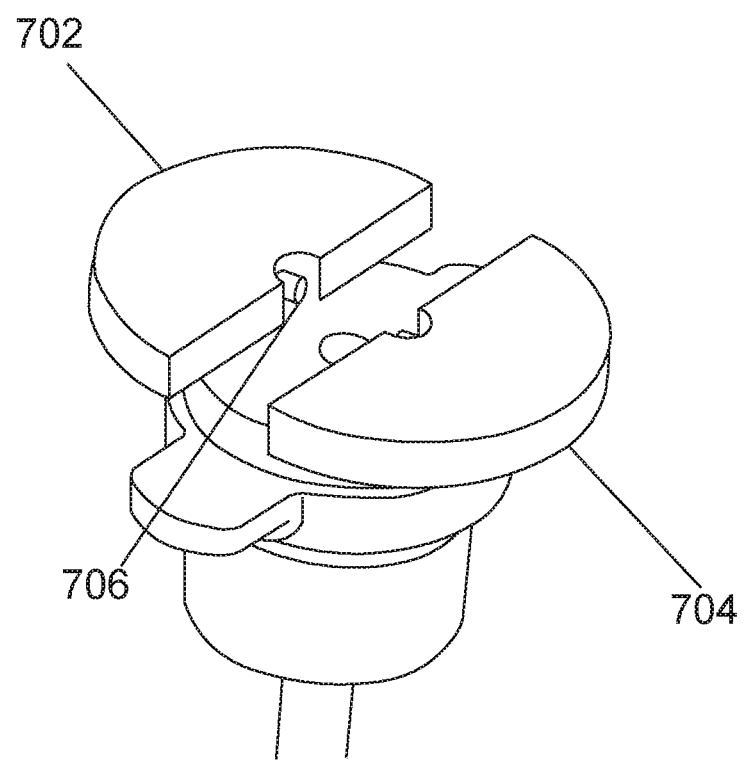
FIG. 7 is a diagram of an external end of an example locking trocar for the "female" instrument in accordance with some implementations.
Figure 8:
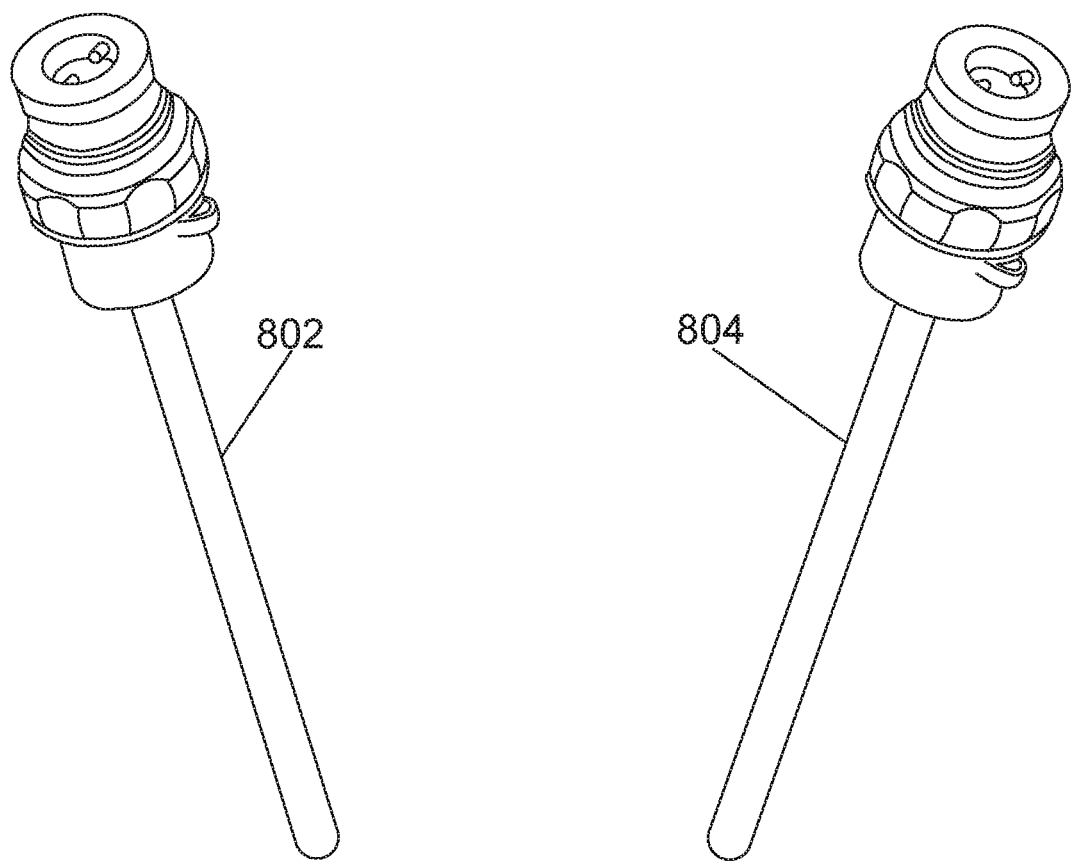
FIG. 8 is a diagram of example locking trocars in accordance with some implementations.

FIG. 3 is a diagram of example locking trocars (202, 204) in accordance with some implementations. The locking trocars (202, 204) shown in FIG. 3 are shown in a locked state. FIGS. 6 and 7 show the locking trocars (202, 204) in an unlocked state. The locking trocars as disclosed herein (e.g., 202, 204) include a hollow tube that enters the body of the patient. Each locking trocar has an exterior opening including two interlocking pieces (e.g., 602/604, and 702/704) that are constructed and configured to pull apart (to an unlocked state) and push back together (to a locked state). One or both of these pieces can have one or more pegs (e.g., 606 or 706) that can fit into one of the holes (e.g., 103 and 105, in FIG. 1) in the retractor instruments to hold the corresponding retractor instrument in place ("peg-in-hole" structure and technique). Once a port is locked, the retractor instrument in that port should be at least partially immobile relative to longitudinal movement within the locking trocar. An instrument locked in place in the locking trocar, though partially or fully immobile with respect to longitudinal movement within the locking trocar, may still be able to make other movements such as articulating, and extending or retracting the mesh net, etc.

Figure 4:
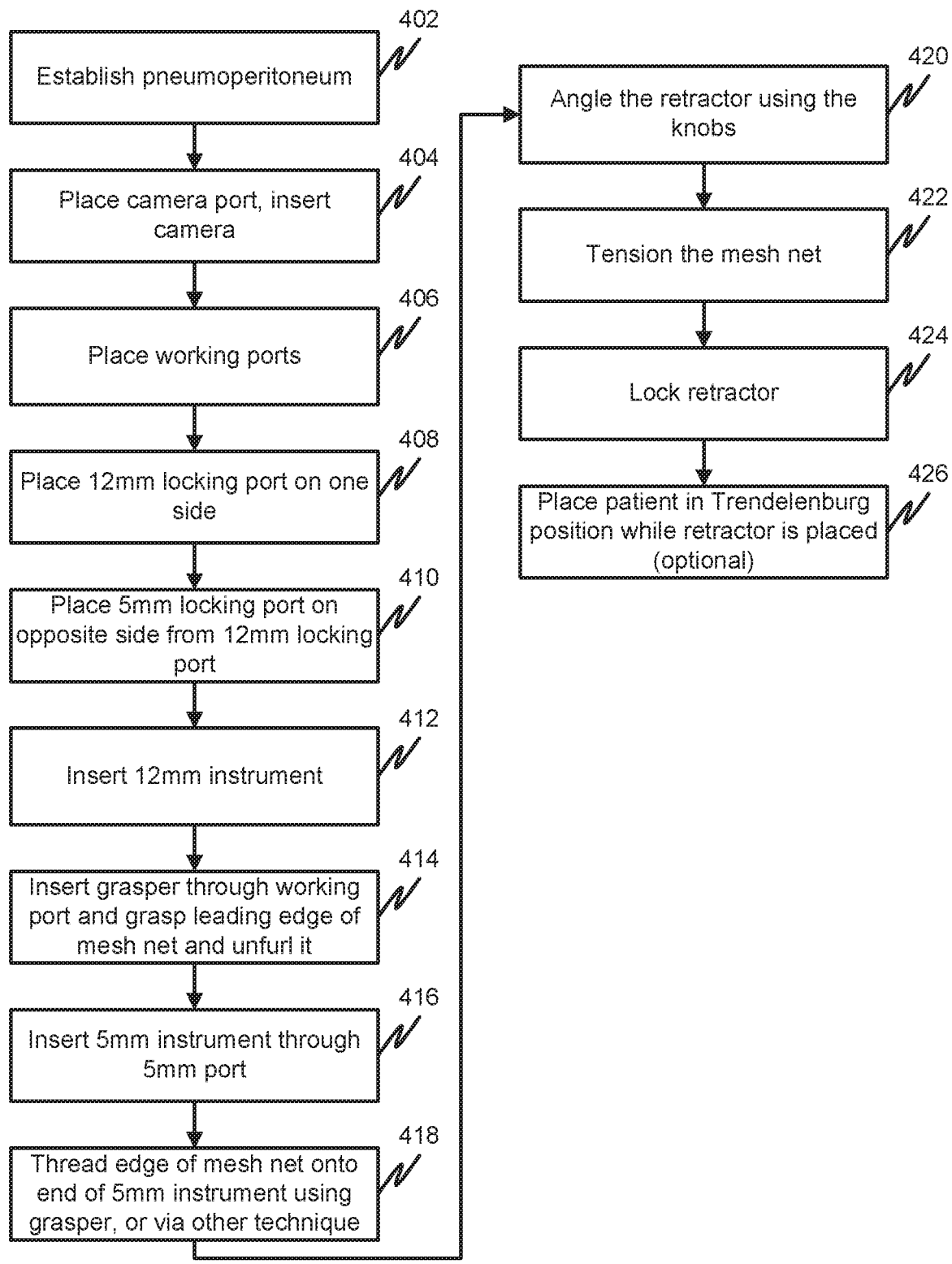
FIG. 4 is a flow chart of a method for retraction in accordance with some implementations.

FIG. 4 is a flow chart of a method for retraction in accordance with some implementations. The method begins at 402, where pneumoperitoneum is established (e.g., with Veress needle or Hassan technique). The method continues to 404.

At 404, a camera port is placed and a camera is inserted into the abdomen via the camera port. The method continues to 406.

At 406, working ports are placed under direct camera vision. The method continues to 408.

At 408, a first "locking" port (e.g., a 5 mm-7 mm or 12 mm port) is placed on one side. The method continues to 410.

At 410, a second "locking" port (e.g., 5 mm-7 mm) is placed on the opposite side from the first port. The method continues to 412.

At 412, a "male" retractor (e.g., the one that houses the mesh or net roll) is brought in through the first port. The mesh or net can be made of plastic or surgical mesh (e.g., silicone, Prolene™, etc.). The method continues to 414.

At 414, a grasper is brought in through one of the working ports and is used to grasp the leading edge of the mesh net and unfurl the mesh net. The method continues to 416.

At 416, the "female" retractor is brought in through the second port. The method continues to 418.

At 418, using the grasper, the leading edge of the mesh net is threaded into a groove at the end of the "female" retractor. The method continues to 420.

At 420, the newly assembled retractor is angled by turning the articulator knob at the top of the instrument (an articulation control knob is present on the exterior end of both "male"/"female" instruments). The method continues to 422.

At 422, the retractor is tensioned by tightening the mesh net by twisting the net control knob on top of the "male" piece (rolling up excess mesh net). The method continues to 424.

At 424, once the retraction is optimal, the retractor is locked into place with the lock mechanism (e.g., a peg-in-hole structure and technique described above with respect to FIGS. 3, 6, and 7) in the locking trocars. The method continues to 426.

At 426, if retraction cannot be easily attained with the patient flat, the patient optionally can be placed briefly in Trendelenburg while the retractor is placed. The patient will then return flat for the remainder of the case. It will be appreciated that 426 can be performed at any point during the procedure.

Figure 5:
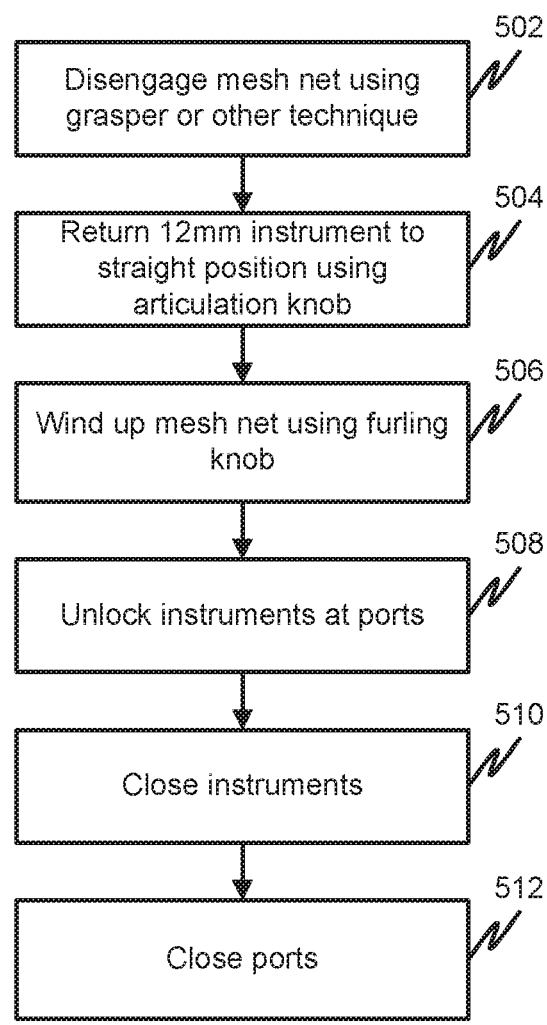
FIG. 5 is a flow chart of a method for retraction in accordance with some implementations.

FIG. 5 is a flow chart of a method for removing retraction in accordance with some implementations. The method begins at 502, where, at the end of the operation, a grasper brought in through a working port disengages the mesh net from the "female" (e.g., 5 mm port) instrument. The method continues to 504.

At 504, the "male" instrument is returned to the straight position by turning the articulator knob. The method continues to 506.

At 506, the mesh net is rolled back up by turning the net control knob until the mesh net is back to its original, wound position. The method continues to 508.

At 508, the instrument is unlocked at the ports. The method continues to 510.

At 510, the instrument is removed. The method continues to 512.

At 512, ports are closed per surgeon choice.

The second instrument can engage or capture the retractor mesh net using various structures and techniques. For example, the mesh net can be manipulated with a laparoscopic grasper to bring it into position to be engaged by the second instrument.

Some implementations can significantly reduce or eliminate Trendelenburg positioning time, and thus help reduce or eliminate the disadvantages of Trendelenburg positioning. This could increase patient safety and can help reduce the costs and time required to prepare a patient for Trendelenburg positioning.

Moreover, by reducing or eliminating Trendelenburg positioning, some implementations can help increase the laparoscopic/robot-assisted candidate population. For example, obese patients and those with pulmonary problems could undergo minimally invasive procedures (e.g., laparoscopic or robot-assisted) more safely.

Currently, retractors may be hand held and thus require an assistant to operate them. Some implementations described herein can be fixed or locked into place, thus reducing or eliminating a need for an assistant to hold the retraction system. Also, the position of one or both instruments of the retraction system described herein can be changed during a procedure when operative conditions change.

It will be appreciated that any dimensions mentioned herein are for purposes of illustrating features and operational aspects of the disclosed subject matter and are not intended to be limiting. Other dimensions could be used.

It will also be appreciated that pelvic surgery (e.g., radical prostectomy) is described herein as an example application of the retraction system and method. Some implementations could be applicable to other types of surgery.

An implementation of the retraction system and/or method described herein could be used for other procedures including, but not limited to, radical prostectomy, radical cystectomy, hysterectomy, sacroculpopexy, low anterior colon resection, and selected herniorrhaphies. Some implementations could be configured for use in various types of surgery including, but not limited to, laparoscopic and/or robot-assisted urological surgery, gynecological surgery, and colorectal surgeries.

It is, therefore, apparent that there is provided, in accordance with the various embodiments disclosed herein, a retraction system and method.

While the disclosed subject matter has been described in conjunction with a number of embodiments, it is evident that many alternatives, modifications and variations would be, or are, apparent to those of ordinary skill in the applicable arts. Accordingly, Applicants intend to embrace all such alternatives, modifications, equivalents and variations that are within the spirit and scope of the disclosed subject matter.

What is claimed is:

1. A retraction system comprising:
   a first instrument including a shaft having one or more locking holes, a first instrument position locking mechanism configured to engage one or more of the locking holes, an articulation control knob to control articulation of an articulated end of the first instrument, a net control knob to control the deployment and retrieval of a net that is configured to be stored within the first instrument and deployed and retrieved in response to control input from the net control knob; and
   a second instrument including one or more locking holes in a shaft of the second instrument, a second instrument position locking mechanism configured to engage one or more of the locking holes, an articulation control knob to control articulation of an articulated end of the second instrument, wherein the articulated end of the second instrument is configured to engage an end of the net and to removably attach to the end of the net.

* * * * *